: United States Patent                    (10) Patent No.:     US 9,915,147 B2
Kyllingstad et al.                                  (45) Date of Patent:         Mar. 13, 2018

(54) METHOD AND APPARATUS FOR REAL-TIME FLUID COMPRESSIBILITY MEASUREMENTS

(71) Applicant: NATIONAL OILWELL VARCO NORWAY AS, Kristiansand S (NO)

(72) Inventors: Age Kyllingstad, Ålgård (NO); Arne Austefjord, Sandnes (NO)

(73) Assignee: National Oilwell Varco Norway AS (NO)

(*) Notice: Subject to any disclaimer, the term of this patent is extended or adjusted under 35 U.S.C. 154(b) by 0 days.

(21) Appl. No.: 14/897,345

(22) PCT Filed: Jun. 19, 2013

(86) PCT No.: PCT/NO2013/050111
§ 371 (c)(1),
(2) Date: Dec. 10, 2015

(87) PCT Pub. No.: WO2014/204316
PCT Pub. Date: Dec. 24, 2014

(65) Prior Publication Data
US 2016/0138393 A1    May 19, 2016

(51) Int. Cl.
*E21B 49/08* (2006.01)
*E21B 49/00* (2006.01)
(Continued)

(52) U.S. Cl.
CPC ............ *E21B 49/005* (2013.01); *E21B 21/08* (2013.01); *E21B 49/00* (2013.01); *F04B 51/00* (2013.01);
(Continued)

(58) Field of Classification Search
CPC ................................................. E21B 2049/085
See application file for complete search history.

(56) References Cited

U.S. PATENT DOCUMENTS 4,255,088 A * 3/1981 Newton ................ A61M 5/365
                                                              417/1
5,635,631 A   6/1997 Yesudas
(Continued)

FOREIGN PATENT DOCUMENTS

EP          2430309         3/2012

OTHER PUBLICATIONS

Written Opinion for PCT/NO2013/050111 dated Mar. 28, 2014 (6 pages).
(Continued)

*Primary Examiner* — Robert R Raevis
(74) *Attorney, Agent, or Firm* — Conley Rose, P.C.

(57) ABSTRACT

Apparatus and method for measuring the compressibility (K) of a fluid circulated by a positive displacement pump that comprises: a pressure sensor for sensing a pressure P of a fluid confined in a fluid module of the pump; a position sensor for sensing the position X, of a piston in the fluid module and a control unit communicating with the pressure sensor and the position sensor adapted to: log the pressure (P) and piston position (X) substantially synchronously; using (X), calculate the volume (V) of the confined fluid in the fluid module; and using (P) and (V), calculate the compressibility (K).

20 Claims, 7 Drawing Sheets

(51) Int. Cl.
 E21B 21/08 (2006.01)
 F04B 51/00 (2006.01)
 G01N 33/28 (2006.01)
(52) U.S. Cl.
 CPC .... *G01N 33/2823* (2013.01); *E21B 2049/085* (2013.01)

(56) References Cited

U.S. PATENT DOCUMENTS

| | | | |
|---|---|---|---|
| 6,176,323 B1 * | 1/2001 | Weirich | E21B 21/08 175/40 |
| 6,832,515 B2 * | 12/2004 | Follini | E21B 47/10 166/100 |
| 7,234,521 B2 * | 6/2007 | Shammai | E21B 49/008 166/264 |
| 2009/0165548 A1 | 7/2009 | Pop | |
| 2013/0243028 A1 * | 9/2013 | Singh | G01N 33/2823 374/43 |
| 2015/0127262 A1 * | 5/2015 | Chen | E21B 49/087 702/2 |

OTHER PUBLICATIONS

Article 19 Amendments to PCT/NO2013/050111 dated Oct. 14, 2015 (2 pages).

\* cited by examiner

METHOD AND APPARATUS FOR REAL-TIME FLUID COMPRESSIBILITY MEASUREMENTS

CROSS-REFERENCE TO RELATED APPLICATIONS

This application is a 35 U.S.C. § 371 national stage application of PCT/NO2013/050111 having the International Filing Date of Jun. 19, 2013 and entitled "Method and Apparatus for Real-Time Fluid Compressibility Measurements," which is hereby incorporated herein by reference in its entirety for all purposes.

STATEMENT REGARDING FEDERALLY SPONSORED RESEARCH OR DEVELOPMENT

Not applicable.

BACKGROUND

Safe managed pressure drilling (MPD) requires a hydraulic model predicting the pressure distribution in a well. The better the model, the more precisely the pressure distribution in the well can be predicted. This hydraulic model should preferably have real-time input of operation parameters, such as top drive speed, weight on bit, pump speed, etc. In addition, actual parameters of the circulated fluid, such as viscosity, density, and compressibility, need to be established, preferably also in real-time. Fluid viscosity and density are both usually measured in the field, e.g. on a drilling rig, and thus are known to drilling operators. Fluid compressibility, on the other hand, is not measured in the field, and is therefore not known by drilling operators, at least not in real-time. Today, fluid compressibility may be found from look-up tables obtained from measurements in remote lab facilities. In order to predict the pressure distribution in the well with a satisfying accuracy, there is a need for a more accurate measurement of compressibility as input to the hydraulic model. The fluid discussed below is drilling mud, but the embodiments disclosed herein have broader application and are applicable to fluids in general, such that the disclosure herein therefore is not restricted to drilling mud.

BRIEF SUMMARY OF THE DISCLOSURE

This disclosure relates to an apparatus for measuring the compressibility of a fluid being circulated by a positive displacement pump. More specifically, there is described an apparatus for measuring the compressibility of a circulated fluid in real-time in a fluid module of a positive displacement pump, the apparatus comprising a pressure sensing device for sensing a pressure of a fluid confined in the positive displacement pump and a position sensing device for sensing the position, directly or indirectly, of a fluid displacing member in the fluid module of the positive displacement pump. The disclosure also relates to a method for measuring the compressibility of a fluid in real-time by means of an apparatus according to the disclosure.

BRIEF DESCRIPTION OF THE DRAWINGS

In what follows a preferred, non-limiting embodiment of the disclosure is depicted on accompanying drawing, where:

FIG. 3b shows an enlarged view of the compression and the decompression phases from the diagram in 3a;

DETAILED DESCRIPTION OF EXEMPLARY EMBODIMENTS

Figure 1:
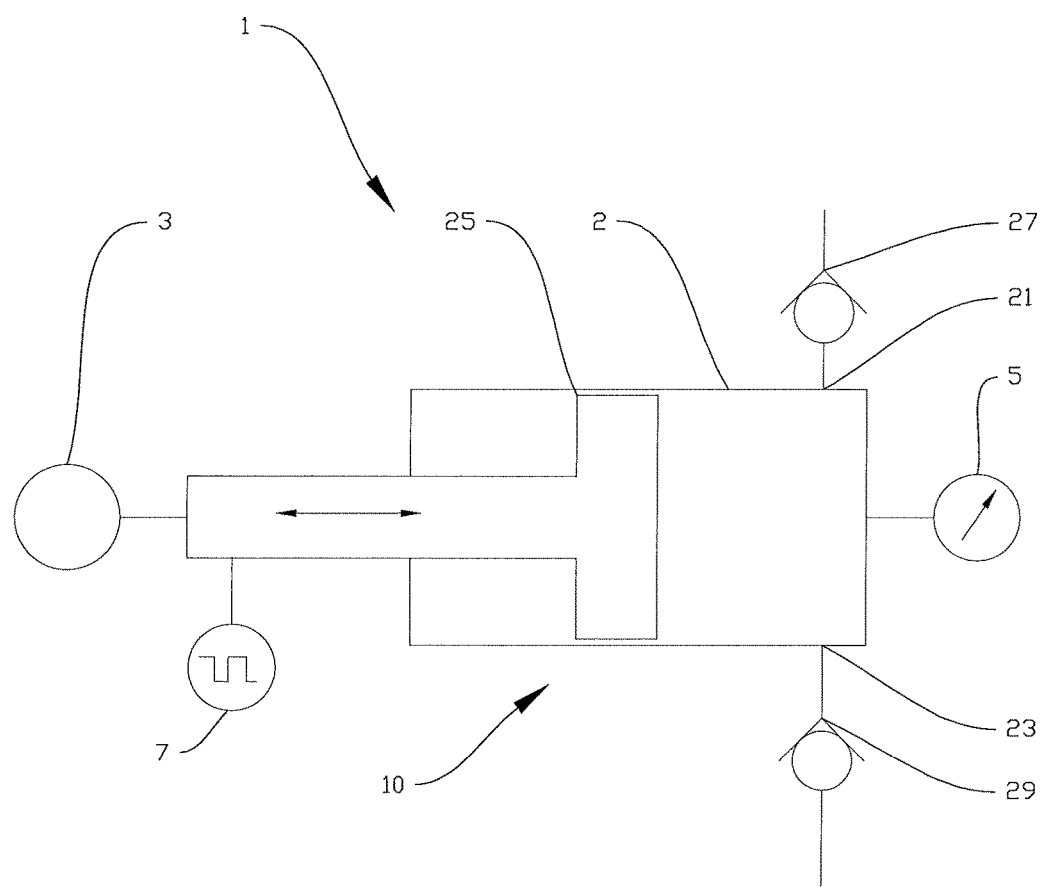
FIG. 1 shows in a schematic drawing an apparatus according to the present disclosure.

In a first aspect, the disclosure relates to an apparatus for measuring the compressibility of a fluid being circulated by a positive displacement pump, the apparatus comprising:
a pressure sensing device for sensing a pressure of a fluid confined in a fluid module of the positive displacement pump;
a position sensing device for sensing the position, directly or indirectly, of a fluid displacing member in the fluid module of the positive displacement pump, wherein the apparatus further comprises a control unit communicating with said pressure sensing device and said position sensing device, the control unit being adapted to:
log said pressure and said piston position substantially synchronously;
by means of the logged position of the fluid displacing member calculate a volume of the confined fluid in the fluid module of the positive displacement pump; and
by means of the logged pressure and the calculated volume, calculate the compressibility of the fluid.

By "fluid module" is meant both the chamber in which the fluid is being compressed/decompressed as well as any the clearance volume.

The positive displacement pump may be a reciprocating piston pump, wherein the fluid displacing member is a piston, and wherein the fluid module comprises the cylinder itself and the clearance volume.

Herein the term "piston pump" shall be construed to also include plunger pumps.

The control unit may be any type of computer, such as a programmable logic controller, a microcontroller or the like. It may be communicating with the sensing devices wirelessly or through cables or other conductors, as will be known to a person skilled in the art.

Compressibility, which is the inverse of the bulk modulus, of a fluid is defined as the ratio of relative volume decrease to change in pressure, in mathematical terms $$K = -\frac{1}{V}\frac{dV}{dP} = -\frac{d(\ln V)}{dP} \quad (1)$$

Here V is the confined fluid volume and P is the fluid pressure. The alternative expression with the natural logarithm of the volume is derived from a well-known rule in differential mathematics. The confined volume in a reciprocating piston pump can be expressed as $$V = V_{max} A \cdot X \quad (2)$$

where X is the piston stroke, referred to the start of the pumping phase, $V_{max}$ represents the maximum volume between the piston and the closed valves, and A is the cross-sectional area of the piston seal. The maximum volume equals the nominal pumping volume ($=A*X_{max}$) plus the residual volume between the valves and the piston in its fully extended position. The residual volume is often called the clearance volume. The piston stroke can be measured either directly by a suitable linear motion sensor such as a linear variable differential transformer, or indirectly by measuring the angular position of the crank shaft or the cam driving the piston. For a crank shaft driven pump, like the commonly-used triplex pump, the piston stroke is given by $$X = (1 - \cos\theta)R + \sqrt{L^2 - (R\sin\theta)^2} - L \quad (3)$$

where R is the crank shaft radius (half the nominal piston stroke), L is the effective crank rod length and $\theta$ is the crank shaft angle, referred to the start of the pumping phase.

The fluid compressibility can therefore be interpreted as the slope of the curve representing $-\ln(V)$ versus pressure P or, alternatively, as the derivative of a fit function matching $-\ln(V)$ versus P. For most fluids, like water based and oil based muds, the compressibility is fairly constant in the pressure range typically experienced when drilling oil or gas wells. For special fluids and/or extreme pressures the non-linearity should not be neglected, meaning that the compressibility changes significantly with pressure.

The combination of formulas 1 and 2 above presumes that both valves are completely closed and that there are no leaks, either in the piston seals or in the valve seals. The compressibility can therefore be determined only in the compression and decompression phases and when all seals are functioning properly. On the contrary, if there is some kind of leak during the transition phases, the method will result in a too high estimated compression and/or in a pronounced non-linear behavior of the calculated compressibility. It is therefore a good practice to calculate a second order compressibility as a means for quality control of the measurement.

Let us assume that the compressibility can vary linearly with pressure. It can then be written as $$K = K_1 + 2K_1 K_2 P \quad (4)$$

Here $K_1$ and $K_2$ are called $1^{st}$ and $2^{nd}$ order compressibility, respectively. The latter is often negative and of the same order of magnitude as the first order compressibility. With this linearly changing compressibility, the equation (1) can be integrated to give the following pressure dependent volume $$V = V_o \exp(K_1 P + K_1 K_2 P^2) \quad (5)$$

The corresponding fluid density is the confined fluid mass divided by the volume, or $$\rho = \rho_o \exp(K_1 P + K_1 K_2 P^2) \quad (6)$$

The subscripts $_o$ in the above formulas refer to zero or standard pressure, most often chosen as 0 barg (=1 atm absolute pressure). Often the compressibility is not tabulated directly, but indirectly as density versus pressure. To convert between density and compressibility, it is useful to perform a series expansion of the exponential function in equation (6). This results in the following approximation, consistent to second order in pressure.

$$\rho = \rho_o \cdot (1 + K + (0.5 K_1 + K_2) K_1 P^2) \quad (7)$$

Density and the compressibility factors are, in general, temperature dependent. Therefore, a precise calculation of the density and the hydrostatic pressure in a well may include thermal expansion effects. It is, however beyond the scope of this document to discuss thermal effects, other than stating that the fluid temperature may preferably be measured also during the described compressibility measurement procedure.

In one embodiment, the control unit may be adapted to log the pressure of the confined volume and the position of the piston at a rate of at least 100 times the rotation frequency of the positive displacement pump. This may enable sufficient loggings in the compression or decompression phase to obtain two or three reliable loggings within the compression and/or decompression phase of the pump in order to be able to calculate the compressibility. The maximum rotation frequency of a positive displacement pump, such as a reciprocating piston pump, may be in the range of 100-300 rpm, thus requiring logging rates of at least 100-300 Hz.

In one embodiment, the pressure sensing device may be adapted to sample the pressure of the confined fluid at a sampling rate of at least 1 kHz. To obtain reliable data, sensing devices should preferable have a higher sampling rate than the desired logging rate. In one embodiment, the sampling rate should be in the range of 10 times the desired logging frequency. A logging frequency of 100 Hz would therefore require a sampling frequency of 1 kHz or above. In one specific, non-limiting embodiment, the pressure sensing device 5 may be a commercially available pressure transmitter, such as a PTX 661 Druck Hammer Union pressure transmitter.

In one embodiment, the control unit, when calculating the compressibility of the confined fluid, may further be adapted to exclude logged data when the pressure of the confined fluid is lower than a pressure $P_{lo}$. As will be described with reference to the drawings later in the description, at low pressure, for instance at the start of the compression phase of the fluid, non-linear effects due to e.g. inertia of valves, compression of gas content in the fluid, compression of piston seal, etc., will be non-negligible. Data logged at pressures below $P_{lo}$ may therefor preferably be excluded from the calculations of compressibility. In one specific, non-limiting example $P_{lo}$ may be in the range of 20 bar.

Similarly, the control unit, when calculating the compressibility of the fluid, may be adapted to exclude logged data when the pressure of the confined fluid is higher than a pressure $P_{hi}$.

In one embodiment, the control unit may be adapted to use regression analysis of the logged data to find the fluid compressibility.

The control unit, when calculating a volume of the fluid, may further be adapted to account for volume changes in the positive displacement pump itself. The volume changes, which may be pressure-induced elastic deformations of the pump, including ballooning of the liner and elastic shortening of the piston rod, may be taken into account for improving the accuracy of the calculated compressibility.

In one embodiment, the apparatus may further comprise a temperature sensing device for sensing the temperature of the fluid in or near the positive displacement pump. The temperature measurements may be taken at the inlet or at the outlet of the fluid pump. The fluid compressibility is, as described above, a temperature-dependent parameter. However, since the fluid parameters are measured in real-time in its flow cycle through the reciprocating pump, the temperature of the fluid will be essentially inherent in the calculated compressibility. Hence, the temperature sensing device should be regarded as an optional feature.

This disclosure also relates to a mud pump comprising an apparatus according to claim 1 of the present application. The mud pump may be any kind of reciprocating pumps commonly used in the oil and gas industry, such as Triplex pumps, Quintuplex pumps or Hex pumps.

In a second aspect, the disclosure relates to a method for measuring the compressibility of a fluid being circulated by a positive displacement pump by means of an apparatus according to claim 1 of the present application, wherein the method comprises the following steps:
 by means of the pressure sensing device, sensing the pressure of a fluid confined in a fluid module of the positive displacement pump;
 by means of the position sensing device, sensing the position, directly or indirectly, of a piston in the fluid module of the positive displacement pump;
 by means of a control unit logging the sensed pressure and position substantially synchronously;
 by means of the logged position of the piston calculating a volume of the fluid confined in the fluid module of the reciprocating pump; and
 by means of the logged pressure and the calculated volume calculating the compressibility of the fluid.

In one embodiment, the method may further comprise sensing the temperature of the fluid in or near the positive displacement pump.

In one embodiment, where the positive displacement pump is a reciprocating piston pump, the method may comprise one or more of following steps:
 1. Measure and record at a high sampling rate cylinder pressure P and angular position $\theta$ of a pump crank shaft or cam;
 2. Calculating a linear piston position X and the corresponding fluid volume V from the angular pump position $\theta$;
 3. Determine a low pressure limit, $P_{lo}$, beyond which a piston seal is completely compressed and a corresponding high pressure limit, $P_{hi}=P_{disch}-P_{lo}$ beyond which one of the valves are partially or fully open, wherein $P_{disch}$ is the discharge pressure of the reciprocating pump;
 4. Selectively pick the compression phase data satisfying the logical function $(P>P_{lo})$ & $(P<P_{hi})$ & $(X<X_{lo})$, where $X_{lo}$ representing maximum compression stroke;
 5. Calculate the help function defined as $Y=-\ln(V)$ and apply regression analysis to the picked data set to find a $2^{nd}$ order polynomial fit function $Y_{fit}=a_0+a_1P+a_2P^2$;
 6. Find the fluid compressibility as the derivative of this fit function and determine the first and second order compressibility as $K_1=a_1-a_s$ and $K_2=a_2/K_1$, respectively. Here $a_s$ is a correction term accounting for pressure induced, elastic deformation of the pump, as explained above;
 7. Accept the compressibility measurement as valid if $K_1$ and $K_2$ are close to their expected values. On the contrary, discard results and flag a possible leak or malfunction of the valves or piston seals; and
 8. Repeat the analysis for the decompression phase data, satisfying $(P>P_{lo})$ & $(P<P_{hi})$ & $(X>X_{hi})$, where $X_{hi}$ represents maximum decompression stroke, typically $X_{max}-X_{lo}$.

It should be understood that several of the above listed algorithm steps are optional, and that the disclosure in its broadest sense is described in the independent claims set out below in the present description The sampling rate may be, as described above, at least 1000 times faster than the highest pump rotation frequency, because the compression and decompression phases represent relatively small fractions of the pump cycle and the regression analysis requires many samples in order to provide statistically robust results.

The elastic deformation correction term can be found either theoretically from detailed knowledge of the pump geometry, or it can be found experimentally from a calibration test where a fluid, with an a priori known compressibility, is used.

The validity check of the derived compressibility parameters could also include the measured compressibility from preceding pump rotations, from other instrumented fluid modules in the same pump, from other pumps pumping the same fluid and/or from consistency between compression and decompression based compressibility estimates. A systematic discrepancy between values derived for the compression and decompression phases, transition phases for short, is an indication that the total volume, is not correct. If the volume is not determined accurately from the internal fluid module geometry of the fluid module, it could be determined experimentally by requiring that the two compressibility estimates match.

Systematic errors and discrepancies between compression and decompression values also arise if the angular shaft position has an offset error. It is therefore important, when using indirect measurement of the piston position that the angular datum position, defined as the start of pump phase, is correct. If it cannot be determined accurately, there is a possibility to determining it experimentally by requiring that the compressibility in the compression and decompression phases match. Such an adjustment requires that there are no leaks and that other parameters are correct.

In the following, the reference numeral 1 refers to an apparatus according to the present disclosure. Identical reference numerals indicated identical or similar features in the figures.

In FIG. 1 an apparatus 1 according to the present disclosure is shown schematically and incorporated into a positive displacement pump 10 in the form a reciprocating piston pump. A fluid module 2, here shown as one simple cylinder, is fluidly connected to an inlet 21 and to an outlet 23. A suction valve 27 is provided at the inlet 21 while a discharge valve 29 is provided at the outlet 23. A fluid displacing member in the form of a piston 25 with a piston shaft 24 is sealingly and reciprocally displaceable in the fluid module 2 by means of a drive unit 3. The piston 25, while being displaced inwardly in the fluid module 2, compresses the fluid confined fined in the fluid module 2 of the reciprocating pump 10 so as to increase the pressure of the fluid. The pressure will be increased up to a level where the discharge valve 29 is opened and mud is discharged from the fluid module 2 through the outlet 23. Correspondingly, when the piston 25 is being displaced outwardly in the fluid module 2, the mud is decompressed. Below a certain pressure level, the suction valve 27 will open and mud will flow into the fluid module 2 through the inlet 21. A position sensing device 7 is shown in the form of a position sensor measuring the position of the piston shaft 24 and thereby the piston 25. By knowing the geometry and the clearance volume of the fluid module 2, the volume V of the mud in the fluid module 2 can be calculated by means of a not shown control unit connected to the position sensor 7 by measuring the exact position of the piston 25 as described in the general part of the description. Further, a pressure sensing device 5 is provided in the fluid module 2. The pressure sensing device 5 is adapted to measure the pressure P of the mud in the fluid module 2 at any position of the piston 25, and transmit the sensed pressure P to the not shown control unit. Thus, pressure sensing device 5 may also be described as a pressure transmitter.

Figure 2:
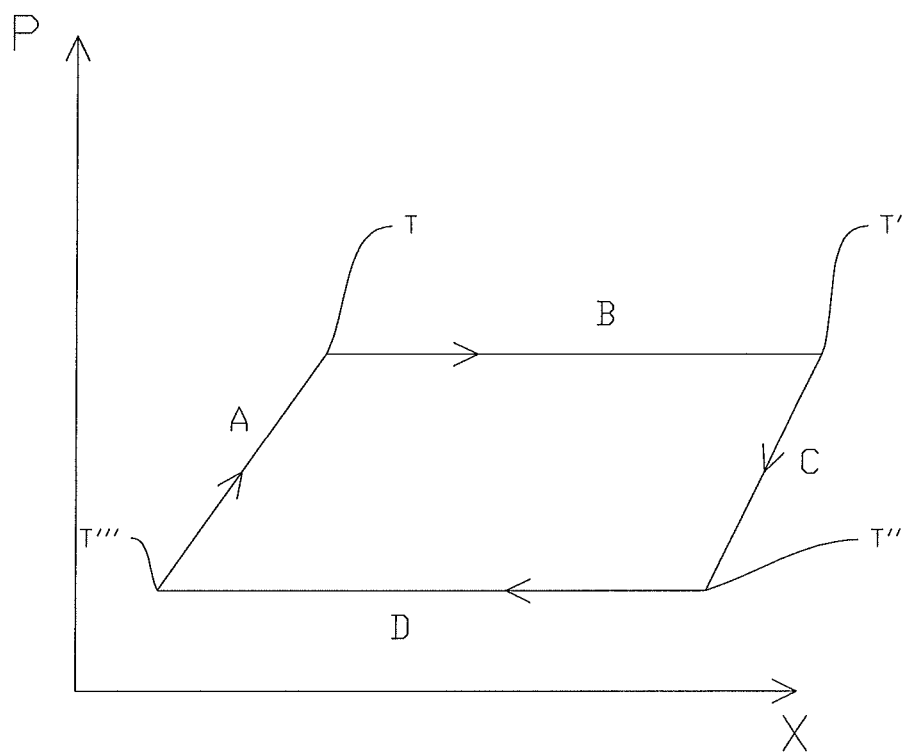
FIG. 2 is a diagram showing the pressure as a function of the position of the piston stroke.

A somewhat simplified example of a curve showing the pressure P of the fluid as a function of the position X of the piston 25 is shown in FIG. 2. In a phase A of the curve, the piston 25 is compressing the fluid. In this simplified example, the compression entails a steadily and linearly increasing pressure P of the fluid. At an abrupt transition T between phase A and a phase B on the curve, the discharge valve 29 is opened while the piston 25 is still being moved inwardly in the fluid module 2. At a second abrupt transition T' between phase B and a phase C, the piston 25 starts moving outwardly/retracting in the fluid module 2, thus decompressing the confined fluid. The pressure P is steadily and linearly decreasing in phase C. The steeper slope of phase C compared to phase A will be explained with reference to FIGS. 3a and 3b below. At a third abrupt transition T''' between phase C and a phase D, the suction valve 27 opens, and the pressure P remains constant in phase D, the suction phase, on the curve as the piston 25 is further retracted while the suction valve 27 remains open. The cycle starts over again at a fourth abrupt transition T''' between phase D and phase A. The position X of the piston 25 is calculated into the volume V of the mud in the fluid module 2, and the compressibility K of the mud can be calculated as described in the general part of the description. Phases A and C of this simplified curve can be used to perform a linear fit to find the compressibility K of the mud. In practical examples, phases A and C may be non-linear as have already been discussed in the general part of the description and will be described with reference to FIGS. 3a and 3b below, and higher order fits may be needed to find the compressibility of the fluid.

Figure 3A:
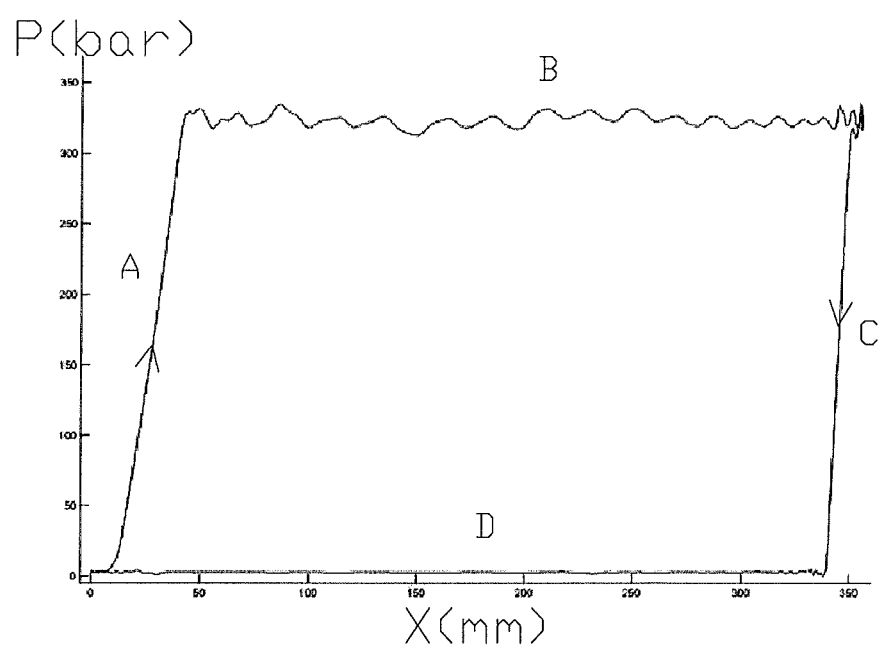
FIG. 3a is a diagram showing the pressure as a function piston stroke of data as measured in a triplex pump.

FIG. 3a shows a cylinder pressure P in bars versus piston stroke X in millimeter recorded in a triplex mud pump. The up- and down arrows in phases A and C indicate, as in FIG. 2, the compression and decompression phases, respectively, suitable for compressibility estimation. The relatively constant high and low level pressure parts in phases B and D of the curve represent pumping and suction phases of the pump 10, respectively, where one of the valves is open. The non-constant discharge pressure $P_{disch}$ is due to pressure variations in a piping system to which the Triplex pump is connected as will be understood by a person skilled in the art. One can also see that the pressure drop in the decompression phase C is steeper than the pressure increase in the compression phase A, which is at least partly due to the fact the whole volume of the fluid module is compressed in phase A, whereas only the clearance volume is decompressed in phase C.

Figure 3B:
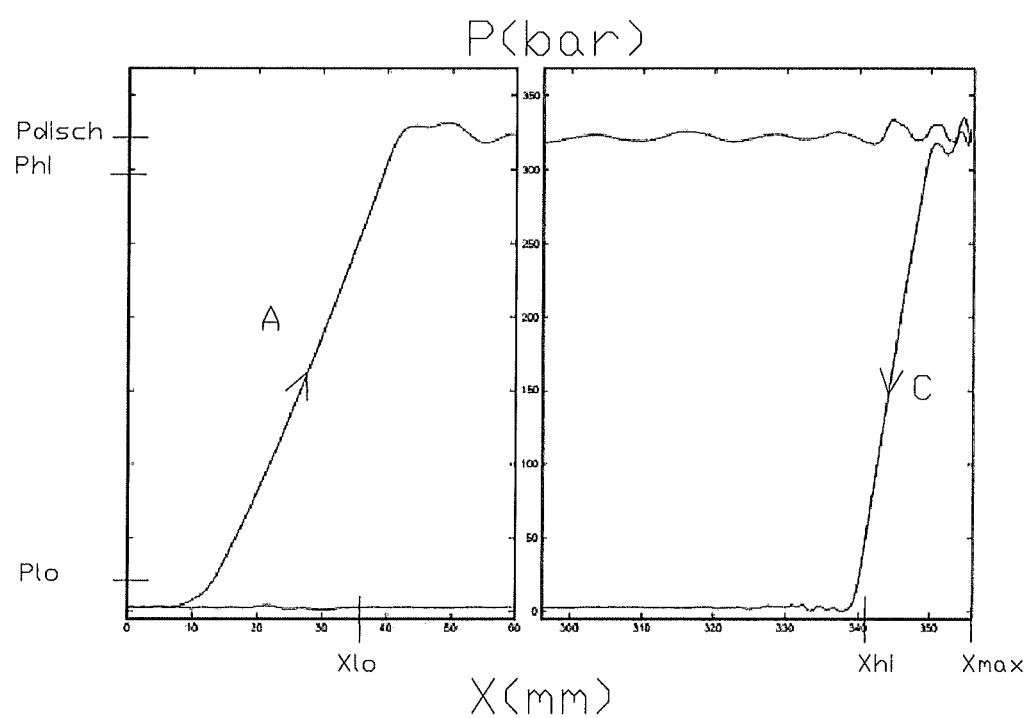

A zoom-in or enlarged plot of the compression and decompression phases A, C is shown in FIG. 3b. The linear compression phase starts slightly after the piston 25 turns and the pressure P has reached a value $P_{lo}$ of roughly 20 bar. This delayed start of the compression phase is due to valve inertia and piston seal compression. Valve inertia causes the discharge valve 29 to close slightly after the piston 25 has passed its datum position, and a cushion effect of the piston seal slows down the fluid compression until there is metal to metal contact between the valve and the valve seat. The resulting low slope part of the compression curve may therefore preferably be excluded from the data used for determining the compressibility K. Similarly, the analysis may exclude pressure data exceed an upper pressure threshold $P_{hi}$, typically equal to the mean discharge pressure $P_{disch}$ minus lower pressure threshold $P_{lo}$. An additional benefit of excluding the lowest pressures in the compressibility calculations is that the disturbing effect of a possible small gas or foam content in fluid will be minimized. As an example, if the gas volume content is 1% at ambient atmospheric pressure, the gas volume has decreased to approximately 0.05% at 20 bar. This is far less than the true fluid compression volume, meaning that the gas will not influence the calculated fluid compressibility significantly. Indicated in the figure are also the pressure values $P_{disch}$, $P_{lo}$ and $P_h$; and the piston stroke values $X_{lo}$, $X_{hi}$, and $X_{max}$ as used in the previously described algorithm, where $P_{disch}$ is the discharge pressure, $P_{lo}$ is the pressure below which logged data may be excluded. $P_{hi}$ is the pressure above which logged data may be excluded, $X_{lo}$ is the maximum compression stroke, $X_{hi}$ is the maximum decompression stroke, and $X_{max}$ is the maximum stroke of the piston 25.

Figure 4:
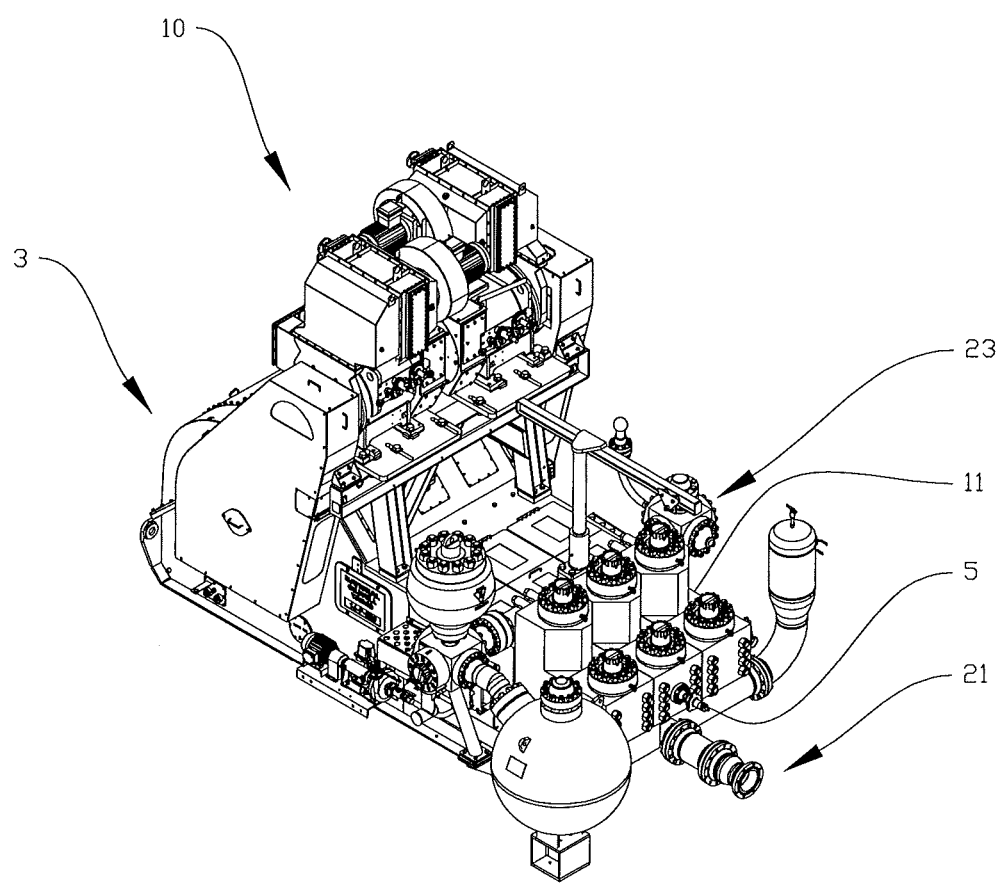
FIG. 4 shows in a perspective view a mud pump according to prior art, to which the pressure sensing device described herein has been incorporated.

FIG. 4 shows a positive displacement pump 10 in the form of a triplex mud pump 10 according to prior art. The shown pump 10 is, minus the pressure transmitter 5, commercially available from the present applicant, and its function and construction will be known to a person skilled in the art and will therefore not be described in detail herein. The triplex mud pump 10 comprises a drive unit 3 connected via not shown cranks to three positive displacements/plungers 25 in cylinders. The position of at least one of the pistons 25 may, according to the present disclosure, be measured by a position sensor 7, not shown in the figure. An inlet 21 in the form of a manifold is fluidly connected to the cylinders through suction valves 27 included in valve blocks 11. Correspondingly the cylinders are fluidly connected to an outlet 23, also in the form of a manifold, through discharge valves 29 in the valve blocks 11.

Figure 5:
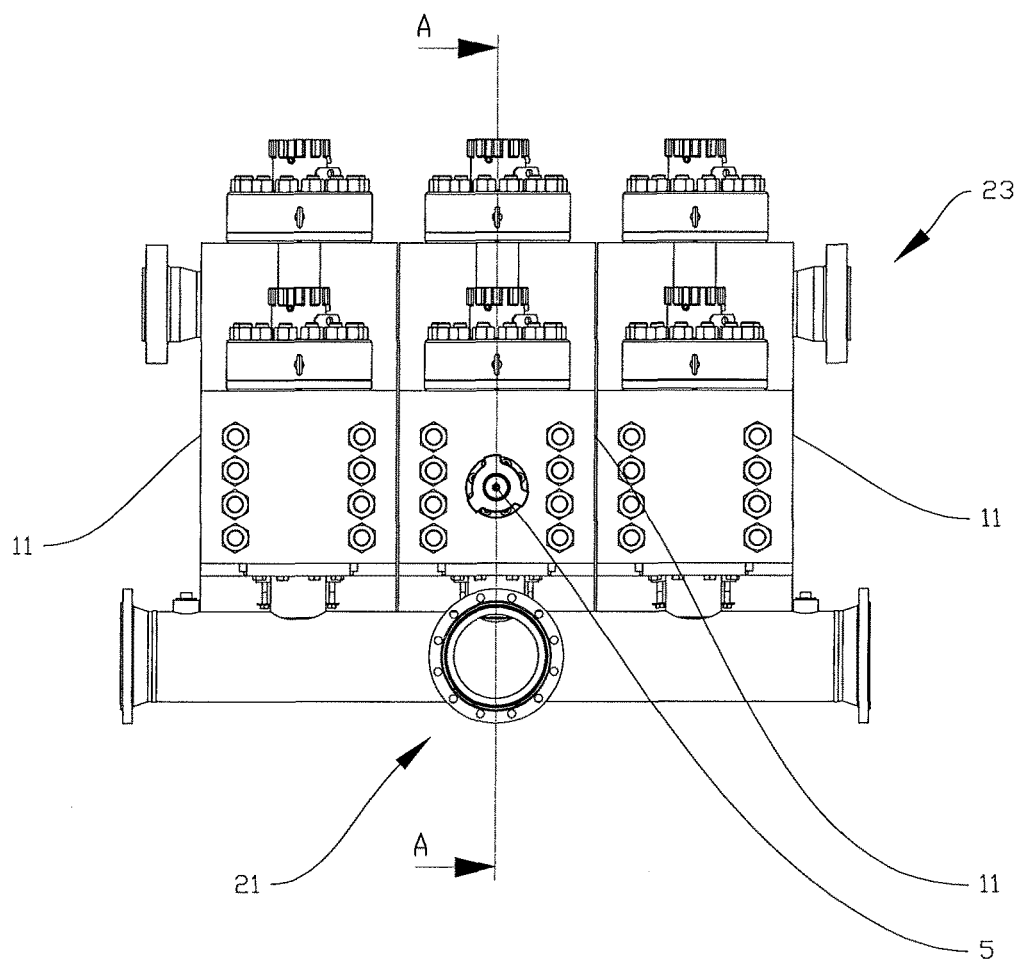
FIG. 5 shows in a front view the valve blocks of the mud pump from FIG. 4 having the incorporated pressure sensing device shown.
Figure 6:
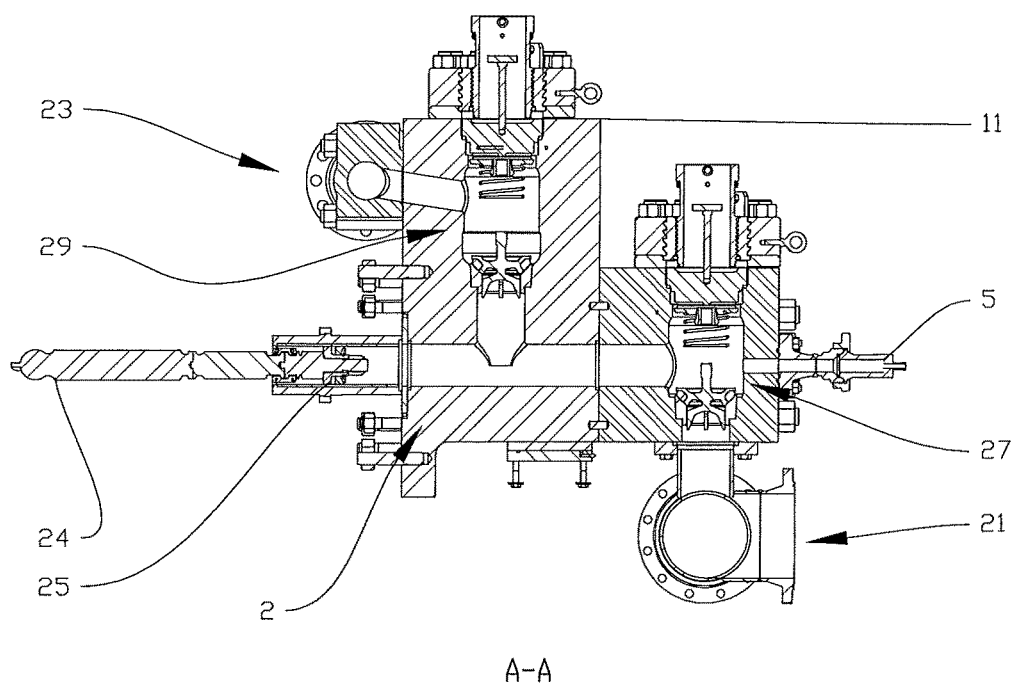
FIG. 6 shows a cross section of the valve blocks and pressure sensing device from FIG. 5 as seen through the line A-A of FIG. 5.

Details of the valve blocks 11, including suction valves 27 and discharge valves 29, are shown in FIGS. 5 and 6. The cylinders and the valve blocks 11 are included in the fluid module 2 of the triplex pump. The pressure transmitter 5 is shown connected to the mid valve block 11. In alternative embodiments, the pressure transmitters 5 can additionally or alternatively be connected to other parts of the fluid module 2.

The invention claimed is:
1. Apparatus for measuring the compressibility (K) of drilling mud being circulated by a positive displacement pump, the apparatus comprising:
a pressure sensing device for sensing a pressure (P) of the drilling mud confined in a fluid module of the positive displacement pump;
a position sensing device for sensing the position (X), directly or indirectly, of a fluid displacing member in the fluid module of the positive displacement pump, wherein the apparatus further comprises a control unit communicating with said pressure sensing device and said position sensing device, the control unit being adapted to: log said pressure (P) and said fluid displacing member position (X) substantially synchronously; by means of the logged position (X), calculate a volume (V) of the confined drilling mud in the fluid module of the positive displacement pump; and by means of the logged pressure (P) and the calculated volume (V), calculate the compressibility (K) of the drilling mud, wherein the control unit is configured to utilize the calculated compressibility (K) to obtain an updated hydraulic model of a well, and utilize the updated hydraulic model of the well to perform managed pressure drilling in the well.

2. Apparatus according to claim 1, wherein the control unit is adapted to log the pressure (P) and the position (X) at a rate of at least 100 times the maximum rotation frequency of the positive displacement pump.

3. Apparatus according to claim 1, wherein the pressure sensing device is adapted to sample the pressure (P) of the confined drilling mud at a sampling of at least 1 kHz.

4. Apparatus according to claim 1, wherein the control unit, when calculating the compressibility (K) of the drilling mud, further is adapted to exclude logged data when the pressure (P) of the confined drilling mud is lower than a pressure $P_{lo}$.

5. Apparatus according to claim 1, wherein the control unit, when calculating the compressibility (K) of the drilling mud, further is adapted to exclude logged data when the pressure (P) of the confined drilling mud is higher than a pressure $P_{hi}$.

6. Apparatus according to claim 1, wherein the control unit further is adapted to use regression analysis of the logged pressure (P) and logged fluid displacing member position (X) to find the drilling mud compressibility (K).

7. Apparatus according to claim 1, wherein the control unit, when calculating a volume (V), is adapted to account for volume changes in the positive displacement pump itself.

8. Apparatus according to claim 1, wherein the apparatus further comprises a temperature sensing device for sensing the temperature of the drilling mud.

9. Apparatus according to claim 1 further comprising a temperature sensing device for sensing the temperature of the drilling mud, and wherein the control unit, when calculating a volume (V), is adapted to account for volume changes in the positive displacement pump itself.

10. Method for measuring the compressibility (K) of drilling mud being circulated by a positive displacement pump comprising:
   sensing the pressure (P) of the drilling mud confined in a fluid module of the positive displacement pump;
   sensing the position (X) of a fluid displacing member in the fluid module of the positive displacement pump;
   logging the sensed pressure (P) and position (X) substantially synchronously;
   by means of the logged position (X) of the fluid displacing member, calculating a volume (V) of the drilling mud confined in the fluid module of the positive displacement pump;
   by means of the logged pressure (P) and the calculated volume (V), calculating the compressibility (K) of the drilling mud;
   utilizing the calculated compressibility (K) to obtain an updated hydraulic model of a well; and
   utilizing the updated hydraulic model of the well to perform managed pressure drilling in the well.

11. Method according to claim 10, wherein the method comprises the step of logging the sensed pressure (P) and position (X) at a rate of at least 100 times the maximum rotation frequency of the positive displacement pump.

12. Method according to claim 10, wherein the method comprises the step of by means of the pressure sensing device sampling the pressure (P) of the confined fluid at a rate of at least 1 kHz.

13. Method according to claim 10, wherein the method comprises the step of excluding logged data from compressibility calculations when the pressure (P) of the confined drilling mud is lower than a pressure $P_{lo}$.

14. Method according to claim 10, wherein the method comprises the step of excluding logged data from compressibility calculations when the pressure P of the drilling mud is higher than a pressure $P_{hi}$.

15. Method according to claim 10, wherein the method further comprises the step of sensing the temperature of the drilling mud.

16. Method according to claim 10, wherein the method further comprises the step of calculating a help function defined as Y=−In ln(V) and applying regression analysis to the picked data set to find a $2^{nd}$ order polynomial fit function $Y_{fit}$=ao+a1P+a2p2.

17. Method according to claim 16, wherein the method further comprises the step of finding the drilling mud compressibility (K) as the derivative of the fit function and determining the first and second order compressibility as $K_1=a_1-a_s$ and $K_2=a_2/K_1$, wherein $a_s$ is a correction term accounting for pressure induced, elastic deformation of the positive displacement pump.

18. Method according to claim 17, wherein the method further comprises:
   determining that $K_1$, and $K_2$ do not fall within a predetermined range of values; and
   setting a flag to note a possible leak or malfunction of the valves or piston seals of the positive displacement pump.

19. Method according to claim 17, wherein the method further comprises the step of accepting the compressibility measurement as valid if $K_1$ and $K_2$ fall within a predetermined range of values.

20. Method according to claim 10, wherein the method further comprises the step of selectively picking decompression phase data satisfying a logical function (P>$P_{lo}$) & (P<$P_{hi}$) & (X>$X_{hi}$), where $X_{hi}$ represents maximum decompression stroke.

* * * * *